United States Patent [19]
Nkiliza

[11] Patent Number: 5,928,646
[45] Date of Patent: *Jul. 27, 1999

[54] PROCESS FOR EXTRACTING CATECHIN POLYPHENOLS FROM POTENTILLAS, EXTRACT OBTAINED AND ITS USE

[75] Inventor: Jean Nkiliza, Port Sainte Foy, France

[73] Assignee: Berkem, Gardonne, France

[*] Notice: This patent issued on a continued prosecution application filed under 37 CFR 1.53(d), and is subject to the twenty year patent term provisions of 35 U.S.C. 154(a)(2).

[21] Appl. No.: 08/829,958

[22] Filed: Apr. 1, 1997

[30] Foreign Application Priority Data

May 30, 1996 [FR] France .................................. 96 06649

[51] Int. Cl.⁶ ..................................................... A61K 35/78
[52] U.S. Cl. ........................... 424/195.1; 424/58; 424/59; 424/78.02; 424/78.03; 424/489; 514/456
[58] Field of Search .................................... 424/195.1, 58, 424/59, 78.02, 78.03, 489; 514/456

[56] References Cited

U.S. PATENT DOCUMENTS

| | | | |
|---|---|---|---|
| 4,698,360 | 10/1987 | Masquelier | 514/456 |
| 5,043,323 | 8/1991 | Bombardelli et al. | 514/25 |
| 5,248,503 | 9/1993 | Emanuel-King | 424/195.1 |

FOREIGN PATENT DOCUMENTS

| | | |
|---|---|---|
| 283349 | 9/1988 | European Pat. Off. . |
| 0348781A1 | 6/1989 | European Pat. Off. . |
| 348781 | 1/1990 | European Pat. Off. . |
| 707005 | 4/1996 | European Pat. Off. . |
| 810222 | 12/1997 | European Pat. Off. . |
| 1427100 | 4/1966 | France . |
| 2092743 | 1/1972 | France . |
| 2372823 | 6/1978 | France . |
| 2643073 | 8/1990 | France . |
| 884184 | 12/1961 | United Kingdom . |

*Primary Examiner*—Jose' G. Dees
*Assistant Examiner*—Kathryne E. Shelborne
*Attorney, Agent, or Firm*—Staas & Halsey LLP

[57] ABSTRACT

A process for extracting essentially oligomeric catechin polyphenols from a potentilla plant, including the steps: treating at least part of the plant with a polar organic solvent to form a first extract, evaporating the first extract to dryness at a temperature of not more than 60° C. to form an evaporation residue, adding water to the evaporation residue to form an aqueous solution, exhaustively extracting the solution with a water-immiscible solvent capable of dissolving oligomeric catechin polyphenols to form an organic solution, evaporating the organic solution to dryness at a temperature of not more than 60° C. to form a second extract of essentially oligomeric catechin polyphenols. The second extract can be used as a compound having a free radical-scavenging action and/or action against UV rays.

13 Claims, No Drawings

PROCESS FOR EXTRACTING CATECHIN POLYPHENOLS FROM POTENTILLAS, EXTRACT OBTAINED AND ITS USE

BACKGROUND OF THE INVENTION

The present invention relates to a process for extracting catechin polyphenols from different Potentilla species, to the extract capable of being obtained by this process and to the use of the extract obtained as active compound in the preparation of pharmaceutical, cosmetic and dietetic compositions.

Many plants are known to contain polyphenols containing oxygen heterocycles, termed "flavonoids" in the broad sense, such as catechins (proanthocyanidins), flavanones, flavonols, anthocyanins and the like. The present invention relates to a process for extracting, from Potentilla, catechin polyphenols or 3-flavanol derivatives, among which epicatechol, catechol and oligomers of these compounds, especially procyanidins, may be mentioned.

According to the invention, the extraction of these catechin polyphenols is carried out from various Potentilla species. Among these species, there may be mentioned tormentil (*Potentilla tormentilla* Neck, also known as *Tormentilla erecta* L., *Tormentilla reptans* L., *Tormentilla officinalis* Curt, *Potentilla tetrapetala* Hall, *Fragaria tormentilla* Granz), silverweed (*Potentilla anserina* L. or *Argentina Vulgaris* Lam.) and cinquefoil or creeping cinquefoil (*Potentilla reptans* L.).

The various Potentilla species, and especially *tormentil*, have already been used in traditional medicine. They were administered in various forms: as powder, decoction or maceration; they were used to treat acute or chronic inflammatory disorders of the gastrointestinal mucosae, or as antiseptics in the form of mouthwashes or gargles, or alternatively to treat pharyngitis.

Moreover, scientific studies have demonstrated the presence of catechin polyphenols in various Potentilla species, especially *Potentilla erecta* L. In this connection, there may be mentioned C.A. 63, 9742 h, which mentions the presence of tannins in *Potentilla erecta*; C.A. T 63, 10314 e, which mentions the presence of myricetin and of leucodelphinidin in *Potentilla erecta* and the presence of ellagic acid in practically all Potentilla species; and C.A. 71, 10266 w, which mentions the presence of (+)-catechol in *Potentilla fruticosa* and *Potentilla anserina* and the presence of (−)-epicatechol in *Potentilla anserina*.

The properties of the potentillas used in traditional medicine are probably due to the presence of catechin polyphenols. Moreover, it is known to use catechin polyphenols, for example extracted from pine bark, in therapy for improving venous wall tonicity, as a vitamin C cofactor or for improving blood circulation. These polyphenols have, in a known manner, free radical-scavenging properties, which enables them to be used in dietetics as a food supplement for preventing atherosclerosis and in cosmetology for combatting cell ageing or the appearance of skin cancers. Furthermore, catechin polyphenols may serve as photoprotective agents on account of their good absorption of ultraviolet light.

Several processes for extracting catechin polyphenols from various plants, such as grape pips and pine bark, have been described in U.S. Pat. No. 4,698,360, EP-A-348, 781, EP-A-283, 349, FR-A-1,427,100, FR-A-2,092,743, FR-A-2,643,073 and FR-A-2,372,823. According to these documents, the plant is treated with water (especially hot water) or a mixture of water and a ketone in variable proportions, and the extract obtained is then treated using a concentrated salt solution so as to precipitate the high molecular weight tannins which are of no therapeutic interest; however, the use of a saline solution is detrimental to the environment and builds an additional cost into the finished product. Carrying out the purification by ultrafiltration through suitable membranes has also been proposed. All of these processes, however, do not permit a catechin polyphenol-rich extract to be obtained from potentillas, especially one which is rich in catechin oligomers and which possesses a sufficiently high degree of purity to be able to be used in man.

SUMMARY OF THE INVENTION

The object of the present invention is to provide a process for extracting catechin polyphenols from potentillas, which does not entail a step of extraction with water, a step of precipitation of the condensed tannins using sodium chloride solution or a step of purification by ultrafiltration, and which enables an extract to be obtained which is rich in catechin polyphenolic compounds of sufficiently high purity to be used in man.

Hence the subject of the present invention is a process for extracting essentially oligomeric catechin polyphenols from potentillas, characterized in that it entails the following steps:

a) the whole plant or a part of the plant is treated with a polar organic solvent, pure or mixed with water, b) the organic extract obtained in step a) is evaporated to dryness at a temperature of not more than 60° C., c) the evaporation residue from step b) is taken up with water, and the aqueous solution obtained is then exhaustively extracted with a water-immiscible solvent capable of dissolving the oligomeric catechin polyphenols, d) the organic solution from step c) is evaporated to dryness at a temperature of not more than 60° C. so as to remove the solvent and obtain a dry extract.

DESCRIPTION OF THE PREFERRED EMBODIMENTS

According to the present invention, in step a), the polar solvent used is preferably a $C_1$–$C_4$ aliphatic alcohol, especially methanol, ethanol, propanol or butanol. When the solvent is mixed with water, it preferably contains not more than 50% by volume of water; the proportions of water are generally between 1 and 30% by volume of water.

The treatment of step a) is preferably carried out at a temperature not exceeding 50° C. and at atmospheric pressure so as to avoid deterioration of the extract of plant origin.

The treatment may be carried out without stirring, but it is preferably carried out with stirring. The time of contact between the plant substance and the solvent must be sufficient to extract the plant substance exhaustively. It is generally between 10 min and 2 hours; a contact time of approximately 1 hour is, more often than not, suitable.

The treatment may be carried out on the whole plant or on a part of the potentilla, especially the rhizome. In the case of silverweed, it is preferable to use the whole plant, and in the case of tormentil and cinquefoil, the rhizome. The choice of the part of the plant treated is dependent on its polyphenol content.

Before treatment with the solvent, the potentilla or potentilla part treated is preferably ground.

In step b) and/or step d), the evaporation is preferably carried out under reduced pressure.

In step c), the water-immiscible solvent capable of dissolving the oligomeric catechin polyphenols is preferably ethyl acetate, but could also be methyl acetate or propyl acetate. The solvent, especially ethyl acetate, is preferably used in a volume substantially equivalent to that of the aqueous phase, and several successive extractions are carried out. In general, four successive extractions are sufficient to extract the aqueous phase exhaustively. The solvent phases are then combined and dried, preferably over an inert drying agent such as anhydrous sodium sulphate or magnesium sulphate. Preferably, after the evaporation residue from step b) has been taken up with water, the aqueous solution obtained is filtered before being exhaustively extracted with the water-immiscible solvent.

In step d), the extract obtained after evaporation to dryness is preferably purified by being taken up with distilled water, and then dried. The drying is advantageously carried out by lyophilization or by atomization.

The dry extract obtained in step d) is a powder which has a beige color and which is completely soluble in water.

The subject of the present invention is also the extract capable of being obtained by the process defined above.

This extract may be used as an active compound in the preparation of pharmaceutical, dietetic or cosmetic compositions having a free radical-scavenging action and/or a protective action against ultraviolet (UV) rays. Their high content of catechin polyphenols enables them, in effect, to be used for the preparation of compositions whose effect is based on their scavenging effect with respect to oxygen free radicals, especially for dermatological use.

It is possible, in particular, to mix the potentilla extract according to the invention with at least one hydroxycinnamic acid of plant origin, described in FR-A-2 734 478, to obtain protection against damage caused by UV through the combined effect of free radical-scavenging properties and screening properties, since it has a very broad spectrum of absorption of UV rays covering the region between 270 and 360 nm. The mixture may be used before, during or after exposure to UV rays, and be administered orally or topically. The potentilla extract obtained by the process according to the invention may be mixed with the hydroxycinnamic acid(s) in proportions ranging from 1% to 80% by weight of acid(s) relative to the total weight of the composition. The additional acid(s) can be chlorogenic acid and its isomers, sinapic acid, ferulic acid, p-coumaric acid and caffeic acid. The additional hydroxy-cinnamic acid(s) is/are preferably extracted from raw coffee.

The example given below, purely as a guide and without implied limitation, will permit a better understanding of the invention.

EXAMPLE

A—Preparation of the extract

Tormentil rhizomes ground in the dry state (17 kg) are treated with stirring using 170 liters of pure methanol, the mixture being maintained at 50° C. After a contact time of approximately 1 hour, the mixture is filtered and the methanolic filtrate is evaporated to dryness at a pressure of 2,000 Pa by heating to a temperature of approximately 40° C. The residue is then taken up with 16 liters of water and filtered. The aqueous solution obtained is exhaustively extracted with ethyl acetate.

Four successive extractions are carried out using at each extraction a volume of ethyl acetate equivalent to that of the aqueous phase. The ethyl acetate phases are combined and then dried over 2 kg of anhydrous sodium sulphate. The ethyl acetate is then removed by evaporation at a pressure of 2,000 Pa at a temperature of approximately 40° C.

The residue obtained is dissolved in 6 liters of distilled water, and the aqueous solution obtained is dried by lyophilization. 0.6 kg of a completely water-soluble beige powder is obtained.

B—Analysis of the constituents of the extract obtained in A

A fraction of the extract obtained in A is peracetylated by the action of pyridine and acetic anhydride while protected from light and at room temperature for 24 hours.

The peracetylated product is subjected to thin-layer chromatography on silica, using a toluene/acetone mixture in a ratio of 8:2 by volume as eluent and a UV lamp at 254 nm for visualization. Three major spots were observed.

A separation of a fraction of the extract on a silica column, with elution with chloroform, was then carried out, and the products corresponding to the three spots were isolated. Their structure was determined by proton and carbon-13 nuclear magnetic resonance (NMR) and by two-dimensional homonuclear and heteronuclear correlation experiments.

The least polar compound (Rf=0.7) is identified as (+)-catechin. That of intermediate polarity (Rf=0.5) is identified as the procyanidin dimer $B_3$ (catechin dimer, linked via the carbons at positions 4 and 8). The most polar compound (Rf=0.3) is identified as a trimer of 3 catechin units linked via the carbon atoms at positions 4 and 8.

C—Determination of the free radical-scavenging activity

The tests were carried out on a culture of NCTC 2544 keratinocytes by a method which enables formation of malondialdehyde (MDA) on exposure to t-butyl hydroperoxide as the oxidizing agent to be measured. MDA is the main product of oxidative degradation of membrane lipids and other cellular components. Measurement of the degree of reduction in MDA formation in cells treated with a product is a good index of the capacity of the product to limit lipid peroxidation.

At a dose of 0.002% weight/volume of cell culture, the tormentil extract obtained in A brings about a significant 18% reduction in MDA production.

D—Determination of the free radical-scavenging activity of a mixture of the tormentil extract obtained in A and an extract of raw coffee The tormentil extract obtained in A and an extract of raw coffee containing 94.5% by weight of chlorogenic acids, including 50% by weight of 5-caffeoylquinic acid, were mixed in equal amounts.

A test employing measurement of the free radical-scavenging activity, as described in C, showed that this mixture, at a dose of 0.002% weight/volume, causes a 39% decrease in MDA production. Measurements carried out with the extract of raw coffee at a dose of 0.5% weight/volume show that the free radical-scavenging activity of the extract of raw coffee alone is negligible: the reduction in MDA production is only 4%.

I claim:

1. Process for extracting oligomeric catechin polyphenols from a potentillas plant, comprising the following steps:
   a) treating at least part of the plant with a polar organic solvent to form a first extract,
   b) evaporating the first extract to dryness at a temperature of not more than 60° C. to form a residue,
   c) adding water to the residue to form an aqueous solution, (d) exhaustively extracting the aqueous solution with a water-immiscible solvent which dissolves oligomeric catechin polyphenols to form an organic solution, and (e) evaporating the organic solution to dryness at a temperature of not more than 60° C. to form a water soluble second extract of the oligomeric catechin polyphenols.

2. The process according to claim 1, wherein step a), comprises using, as the polar organic solvent, a $C_1$–$C_4$ aliphatic alcohol.

3. Process according to claim 1, wherein step a), comprises mixing the polar organic solvent with an amount of water between 1 and 50% by weight.

4. Process according to claim 1, wherein at least one of steps b) and d) is carried out under reduced pressure.

5. Process according to claim 1, wherein a duration of step a) is between 10 minutes and 2 hours.

6. Process according to claim 1, wherein in step a) the at least part of the plant is ground before treatment with the polar organic solvent.

7. Process according to claim 1, wherein step c), comprises using, as the water-immiscible solvent, a $C_1$–$C_3$ alkyl acetate.

8. Process according to claim 1, further comprising the step of using ethyl acetate, in a volume substantially equivalent to that of the aqueous solution, as the solvent in step c), and several successive extractions are carried out in step c).

9. Process according to claim 1, wherein at least one of steps b) and d), comprises using an inert drying agent for evaporating the solvents.

10. Process according to claim 1, further comprising the steps of purifying the second extract using distilled water, and drying the purified second extract.

11. Extract containing essentially oligomeric catechin polyphenols, capable of being obtained by the process according to claim 1.

12. Process for extracting oligomeric catechin polyphenols from a potentillas plant, comprising the following steps:

(a) treating at least part of the plant with an organic solvent, to form a first extract, (b) evaporating the first extract to dryness at a temperature of not more than 60° C. to form a residue, (c) adding water to the residue to form an aqueous solution, (d) adding to the aqueous solution a water-immiscible solvent which dissolves oligomeric catechin polyphenols to form an organic solution, (e) evaporating the organic solution at a temperature of not more than 60° C. to form a water soluble second extract of the oligomeric catechin polyphenols, and (f) adding the second extract as an active compound in a pharmaceutical, dietetic or cosmetic composition to impart free radical-scavenging properties and/or UV ray protection properties.

13. The process according to claim 12, further comprising the step of mixing the second extract, with at least one hydroxycinnamic acid.

* * * * *